United States Patent [19]

Larsson et al.

[11] 4,191,646

[45] Mar. 4, 1980

[54] APPARATUS FOR CONDUCTING FLUIDS IN A DIALYSIS SYSTEM

[75] Inventors: Lars-Åke L. Larsson, Löddeköpinge; Lars J. C. Travén, Lund, both of Sweden

[73] Assignee: Gambro AB, Sweden

[21] Appl. No.: 841,896

[22] Filed: Oct. 13, 1977

[30] Foreign Application Priority Data

Oct. 14, 1976 [SE] Sweden ............................ 7611387

[51] Int. Cl.² .......................................... B01D 31/00
[52] U.S. Cl. ................................ 210/103; 210/137; 210/149; 210/181; 210/321 B
[58] Field of Search ............... 210/85, 90, 137, 143, 210/149, 181, 321 B, 103, 321 HT; 137/517; 165/32, 40, 46, 96

[56] References Cited

U.S. PATENT DOCUMENTS

| | | | |
|---|---|---|---|
| 3,457,944 | 7/1969 | Cary et al. | 137/341 |
| 3,474,907 | 10/1969 | Cary et al. | 210/103 |
| 3,485,245 | 12/1969 | Lahr et al. | 165/46 |
| 3,508,656 | 4/1970 | Serfass et al. | 210/103 |
| 3,590,215 | 6/1971 | Anderson et al. | 165/46 |
| 3,669,880 | 6/1972 | Marantz et al. | 210/22 |
| 3,722,680 | 3/1973 | Smith | 210/96 |
| 3,774,762 | 11/1973 | Lichtenstein | 210/94 |
| 3,827,975 | 8/1974 | Bizot et al. | 210/22 |
| 3,830,676 | 8/1974 | Elkins | 156/289 |
| 3,909,377 | 9/1975 | Bizot et al. | 204/95 |

FOREIGN PATENT DOCUMENTS

364633 3/1974 Sweden.

OTHER PUBLICATIONS

Chemical Engineers Handbook, R. H. Perry et al., 5th Edition, McGraw-Hill Book Co., 1973, pp. 22/39-22/41.

*Primary Examiner*—Thomas G. Wyse
*Assistant Examiner*—David R. Sadowski
*Attorney, Agent, or Firm*—Lerner, David, Littenberg & Samuel

[57] ABSTRACT

Fluid conducting apparatus is disclosed for a dialysis system having a dialyzer, a source of dialysis fluid for the dialyzer, a heating chamber for heating dialysis fluid before introduction into the dialyzer, and pump means for pumping heated dialysis fluid from the heating chamber to and through the dialyzer. The fluid conducting apparatus includes first and second fluid conducting means. The first fluid conducting means is adapted to be connected to the source of dialysis fluid and to the heating chamber for introducing dialysis fluid into the heating chamber, and the second fluid conducting means is adapted to be connected to the heating chamber, the dialyzer and the pump means for conducting the fluid from the heating chamber to and through the dialyzer. The apparatus also includes shut-off means adapted to terminate the flow of heated dialysis fluid from the heating chamber to the dialyzer when the rate of flow of fluid out of the chamber exceeds the rate of flow of fluid into the chamber. In this way, the heating chamber will not be emptied of dialysis fluid.

19 Claims, 3 Drawing Figures

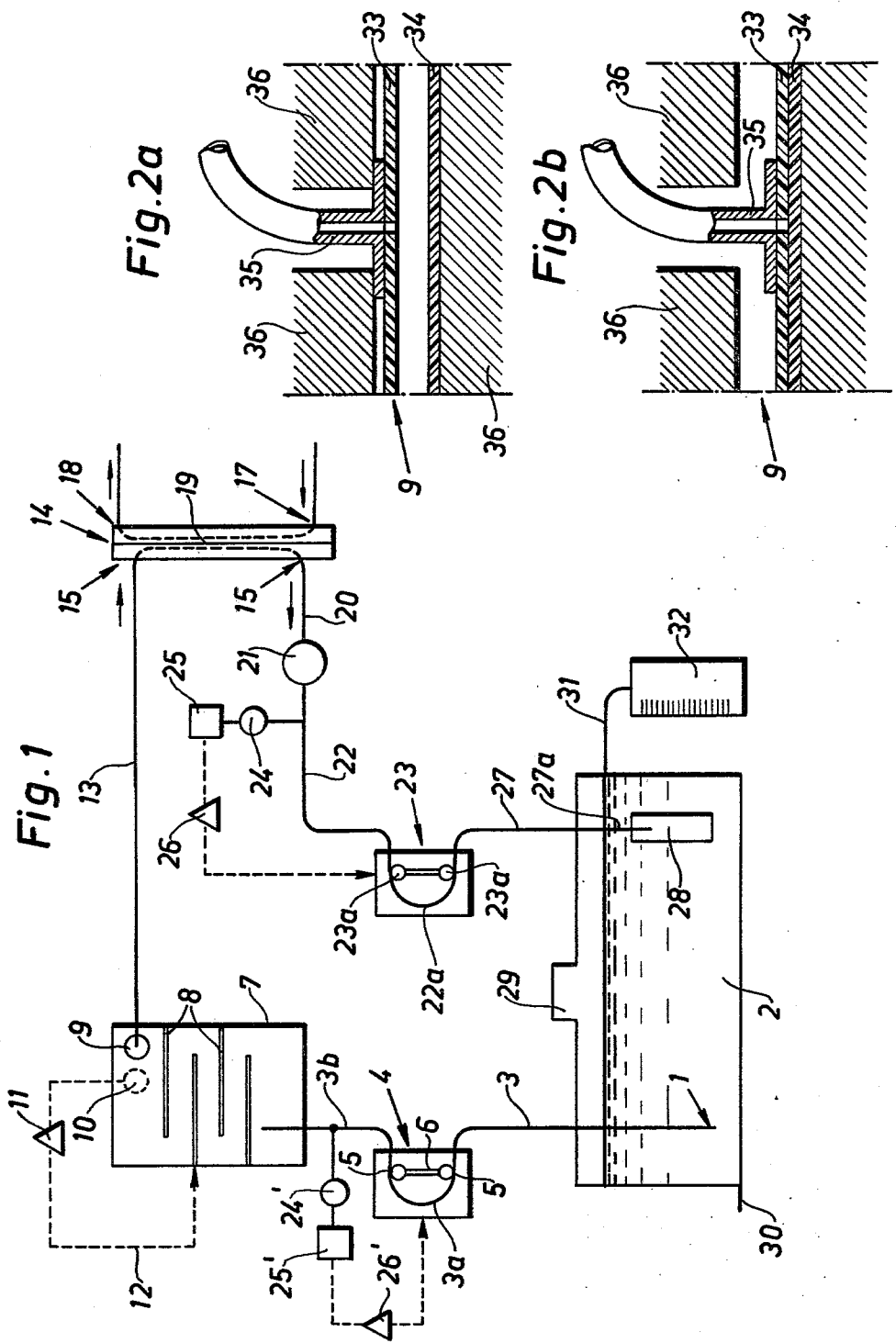

APPARATUS FOR CONDUCTING FLUIDS IN A DIALYSIS SYSTEM

BACKGROUND OF THE INVENTION

The present invention relates to apparatus for conducting fluids in a dialysis system.

A dialysis system normally comprises a dialyzer for treating a first fluid, e.g. blood, with a dialysis fluid, the dialyzer including a dialyzing membrane which separates the fluid to be treated and the dialysis fluid. The system also normally includes a source of dialysis fluid, a heating chamber in which the dialysis fluid is heated before being introduced into the dialyzer, and a pump for pumping the heated dialysis fluid from the heating chamber to and through the dialyzer, and from there to a drain or a regrenating device.

The flow of dialysis fluid from the source to the heating chamber where it is to be heated can be accomplished by means of a line which is adapted to transport the fluid by means of gravity. Preferably however, a pump is used to pump the dialysis fluid from the source to the heating chamber in order to insure a steady flow of dialysis fluid into the heating chamber. As noted above, heated dialysis fluid is withdrawn from the heating chamber and conducted to the dialyzer by means of a pumping device, which in a normal instance is located downstream of the dialyzer. As can be appreciated, as two different means or devices are used for transporting dialysis fluid from the source to the heating chamber and from the heating chamber to the dialyzer, a difference in transport rates can result in either the heating chamber being emptied of heated dialysis fluid or too much fluid being pumped into the heating chamber. This in turn can result in a non-uniform flow of dialysis fluid to the dialyzer as well as a non-uniform heating of same. Further, if the heating chamber is emptied of fluid, the chamber can be damaged beyond repair by the heating means which may continue to operate.

These and other disadvantages of the prior art are overcome by the present invention.

SUMMARY OF THE INVENTION

The fluid conducting apparatus of the present invention is adapted to be employed in connection with a dialysis system having a dialyzer, a source of dialysis fluid, a heating chamber for heating dialysis fluid prior to its introduction into the dialyzer, and pump means for conducting heated dialysis fluid from the heating chamber to and through the dialyzer. The fluid conducting apparatus comprises first fluid conducting means adapted to be connected to the source of dialysis fluid and to the heating chamber for introducing dialysis fluid into the heating chamber, and second fluid conducting means adapted to be connected to the heating chamber, the dialyzer and the pump means for conducting fluid from the heating chamber to and through the dialyzer, and shut-off means adapted to terminate the flow of heated dialysis fluid out of the heating chamber if the rate of flow of fluid out of the heating chamber exceeds the rate of flow of fluid into the heating chamber. In this way, the heating chamber is prevented from being completely emptied of dialysis fluid.

The present invention also comprises an improved container for fluids which is adapted to prevent emptying of fluid therefrom, and which is useful as the heating chamber of a dialysis system. The fluid container of the present invention thus comprises a collapsable member having first and second flexible wall portions, an inlet for introducing fluid into the member, withdrawing means for withdrawing the fluid from the member comprising an opening in the first flexible wall portion, and the first and second wall portions being juxtaposed to one another and being free to move between an open, separated position and a closed, abutting position so that when the amount of fluid being withdrawn from the member exceeds the amount of fluid being introduced into the member, the first and second flexible wall portions are caused to move towards the closed, abutting position to prevent the member from being completely emptied from fluid.

Thus, in a preferred embodiment of the fluid conducting apparatus of the present invention, the heating container comprises a collapsable member having an inlet for introducing dialysis fluid into the member and an outlet for withdrawing fluid from the member, and the shut-off means comprises first and second flexible wall portions of the collapsable member with the outlet being positioned in the first flexible wall portion. The first and second wall portions are juxtaposed to one another and are free to move between an open, separated position and a closed, abutting position so that when the amount of fluid being withdrawn from the collapsable member exceeds the amount of fluid being introduced thereinto, the first and second flexible wall portions are caused to move toward the closed, abutting position whereby the outlet in the first flexible wall portion is closed by the second flexible wall portion to prevent complete emptying of dialysis fluid out of the member.

These and other features and characteristics of the present invention will be described in more detail with reference to the enclosed drawing which shows diagramatically and by way of example the preferred embodiment of the present invention. For the sake of clarity, any details known to those versed in the art and not essential for the understanding of the present invention, have not been included. Further, it should be noted that, as the present invention is mainly intended for use with dialysis systems in general, it will be described with reference to such an application. However, to those versed in the art, it will be clear that the present invention may also be applied to other fields.

BRIEF DESCRIPTION OF THE DRAWINGS

FIG. 1 is a schematic diagram of the fluid conducting apparatus in accordance with the present invention together with certain elements of the dialysis system to which it is adapted to be connected.

FIGS. 2a and 2b are cross sectional views of a valve unit according to the present invention, illustrating the valve unit in open and closed positions respectively.

DETAILED DESCRIPTION OF THE PRESENT INVENTION

Referring to FIG. 1, there is shown diagrametically flow conducting apparatus according to the present invention together with the dialysis apparatus with which it intended to be used. This flow conducting apparatus may for example, comprise a plurality of tubes or lines which are adapted to be connected to the various elements of the dialysis system. In FIG. 1, an inlet 1 of line 3 is connected to a source of dialysis liquid. This source consists in the example shown of a vessel 2 which, for example, may have a sack-like shape.

From the inlet 1, the dialysis liquid is conducted via line 3 to a pump 4. This pump may consist, for example, of a normal rotary pump known in itself, in which a part of the line 3a is alternately compressed by two rollers which are arranged jointly on a rotating arm 6. An example of such a pump is described in U.S. Pat. No. 3,515,275 and is therefore not discussed in any detail here.

From the pump 4 dialysis liquid is pumped via the line section 3b to a heating container 7. This heating container 7 may take any form but preferrably has the form of a simple bag of plastic or other flexible material which is readily compressed. This bag is intended in a manner known in itself, to be placed between two heating surfaces for warming up. For example, the heating device may consist of two plane heating plates 36 (partially shown in FIGS. 2a and 2b) arranged opposite one another, which between them compress the heating container 7. In order to lengthen the flow path through the bag, it is welded or glued together along the lines 8. Numeral 9 designates an outlet valve which will be described in greater detail hereinbelow. Directly before the outlet valve 9 the bag is provided with a temperature transmitter 10 which can be connected to a temperature controller 11 which in turn controls the temperature of the heating arrangement to which the container 7 is adapted. This can take place in a manner known in itself and has therefore only been indicated by the arrow 12 in broken line in FIG. 1.

From the outlet valve 9 the dialysis liquid is conducted via the line 13 to a dialyzer 14 shown schematically. The inlet for the dialysis liquid is marked 15 and the outlet 16. Similarly, the inlet for blood or other fluid to be treated is marked 17 and the outlet 18. Numeral 19 designates a membrane shown schematically which in the dialyzer 14 separates the dialysis liquid from the blood or corresponding liquid. More accurately described constructions of this type are shown for example in U.S. Pat. Nos. 3,411,630 and 3,516,548.

From the outlet 16 of the dialyzer 14 the dialysis liquid is conducted via line 20 to a blood detector 21. This blood detector 21 may simply consist of a transparent part of the tube 20 placed in front of a photocell monitor. In case of any blood appearing in the line 20, a warning signal may be given off or the whole system may be shut down. Such a system too is known, however, and need not be described in detail here. The dialysis liquid then passes through line 22 to a pump 23 which may be of the same construction as pump 4. A part 22a of the line 22 is thus alternately pressed together by the schematically shown rollers 23a. The dialysis liquid is them pumped via the line 27 back to the vessel 2 via a regenerating device 28, connected to the outlet 27a. The regenerating device 28 is for the purpose of cleaning the dialysis fluid so that the dialysis fluid may again be used in the dialyzer 14. Such an arrangement in turn allows the liquid vessel 2 to be of a smaller size. The regenerating device 28 may, by way of example, be in the form of a charcoal cartridge or the like.

In order to prevent any unfavorable effect on dialysis treatment of closing or opening of the outlet valve 9 (the structure and operation of which will be described below), the flow conducting apparatus of the present invention preferably either includes or is adapted to be connected to a pressure stabilizing device for maintaining a substantially constant pressure across the dialyzer, whether or not the valve 9 is closed. In FIG. 1, this is accomplished by means of a pressure gauge 25 being placed in a connecting line 24 to measure the pressure in the line 22. In response to the pressure measured by gauge 25, a pressure controller 26 acts to control the capacity of the pump 23 to maintain a substantially constant pressure in line 22. The connector 24 can be such as to prevent dialysis fluid from coming into direct contact with the pressure gauge 25 and contaminating same. Such a connector is described in Swedish Pat. No. 365,633. In the system depicted in FIG. 1, the controller 26 acts to directly control the speed of the pump 23. Alternatively, it is possible to control the capacity of the pump 23 by variation of a valve in a shunt line arranged to by-pass the pump. However, such shunt line has not been indicated in FIG. 1.

Likewise, the pump 4 may be appropriately controlled in the same manner as the pump 23 via a connector 24′, a pressure gauge or pressure monitor 25′, and a controller 26′ to control and/or stabilize the pressure of the dialysis fluid pumped to the heating container 7. The main purpose behind such an arrangement is to prevent any bursting of the heating container 7 due to excessive pressure.

Preferably all the parts of the fluid conducting apparatus of the present invention which come into contact with the dialysis liquid are in the form of a one-way or disposable unit which as a unit can readily be connected to or disconnected from the fixed components of the dialysis system such as pumps, pressure gauges, pressure controllers, thermometers, etc. Further, this one-way or disposable unit may also include the large liquid vessel 2 containing the whole of the dialysis liquid which is required for treatment.

The liquid vessel 2 may be filled with an appreciable quantity of dialysis liquid, such as for example through inlet 29. Further, as it may be appropriate to empty the vessel 2 before it is destroyed, together with the remaining one-way or disposable components such as for example, by burning, the vessel 2 is provided with an outlet 30. Moreover, the vessel 2 is provided with a spillway 31 which leads to a smaller vessel 32. In this vessel 32, ultra filrate may be collected and measured easily if the liquid level in vessel 2 is raised up to the spillway 31 before the dialysis treatment is begun.

In FIGS. 2a and 2b the valve 9 of the present invention is shown in greater detail. FIG. 2a shows the valve in open position and FIG. 2b shows the same in closed position. Numerals 33 and 34 designate opposite flexible walls of the heating container 7. To the wall 33, a connecting nozzle 35 has been welded or attached in some other manner and throughwhich heated dialysis fluid in the container 7 may be withdrawn. This nozzle 35 together with the adjoining part of the wall 33 serves as a valve seat, whilst the opposite wall 34 serves as a shut-off element. The two walls 33,34 are juxtaposed from one another and by virtual of the walls 33, 34 being flexible, are free to move between an open separated position (shown in FIG. 2a), and a closed, abutting position (shown in FIG. 2b) in which the opening through wall 33 and nozzle 35 is closed by wall 34. In the preferred embodiment, the portions of walls 33 and 34 adjacent to and opposite the outlet are planar and parallel to one another. The closed, abutting position of the walls 33, 34 is obtained when the heating container 7 collapses, which it does when more liquid is pumped out of the container 7 via the line 13 than is pumped into the same via the line 3b. Similarly, if dialysis fluid is introduced into the container 7 by means of gravity, the container 7 will collapse if more fluid is withdrawn from the container 7 than is supplied by gravity. Numeral 36, finally, designates the inner wall of the heating device (otherwise not shown) for the container 7.

Naturally, the invention is not limited solely to the example described above, but can be varied within the scope of the following claims. For example, the details shown schematically in FIG. 1 can be varied within wide limits both in respect of shape and construction. Certain components can also change place in the system. For example, the regenerating device 28 may alternatively be placed in the inlet 1 of line 3.

What is claimed is:

1. Apparatus for conducting fluids in a dialysis system having a dialyzer, a source of dialysis fluid for the dialyzer, heating means for heating dialysis fluid before introduction into the dialyzer, and pump means for pumping heated dialysis fluid to and through the dialyzer, said fluid conducting apparatus comprising:
   a heating chamber for cooperation with said heating means to heat fluid introduced into said heating chamber, said heating chamber comprising a collapsible member having an inlet for introducing dialysis fluid into said collapsible member and an outlet for withdrawing fluid from said collapsible member;
   first fluid conducting means for connection to the source of dialysis fluid and to said inlet of said heating chamber collapsible member for delivering dialysis fluid from the source of dialysis fluid to said heating chamber collapsible member;
   second fluid conducting means for connection to said outlet of said heating chamber collapsible member, the dialyzer, and the pump means for conducting fluid from said heating chamber collapsible member to and through the dialyzer; and
   shut-off means associated with said second fluid conducting means for terminating the flow of fluid from said heating chamber collapsible member to the dialyzer to prevent the emptying of fluid from said heating chamber collapsible member, said shut-off means comprising first and second flexible wall portions of said heating chamber collapsible member, said first and second flexible wall portions being juxtaposed to one another and arranged to be free to more between an open, separated position and a closed, abutting position, and said outlet of said heating chamber collapsible member being positioned in said first flexible wall portion so that when the amount of fluid being withdrawn from said heating chamber collapsible member exceeds the amount of fluid being introduced into said heating chamber collapsible member and the amount of fluid in said heating chamber collapsible member falls below a predetermined value, said first and second flexible wall portions are caused to move towards said closed, abutting position whereby said second flexible wall portion closes said outlet in said first flexible wall portion.

2. The apparatus of claim 1 wherein said flexible wall portions are planar and parallel to one another.

3. The apparatus of claim 1 wherein said first fluid conducting means, said second fluid conducting means and said shut-off means are disposable.

4. An improved dialysis system for treating a first fluid with dialysis fluid, the system comprising:
   a dialyzer in which the treatment occurs;
   a source of dialysis fluid for said dialyzer;
   a heating chamber having heating means for heating the dialysis fluid before being conducted to said dialyzer, said heating chamber comprising a collapsible member having an inlet for introducing dialysis fluid into said collapsible member and an outlet for withdrawing fluid from said collapsible member;
   first fluid conducting means for delivering dialysis fluid from said source of dialysis fluid to said heating chamber collapsible member;
   second fluid conducting means for conducting fluid from said heating chamber collapsible member to and through said dialyzer;
   first pump means in said second fluid conducting means for pumping through said second fluid conducting means dialysis fluid from said heating chamber collapsible member to and through said dialyzer; and
   shut-off means associated with said second fluid conducting means for terminating the flow of fluid from said heating chamber collapsible member to said dialyzer to prevent emptying of fluid from said heating chamber collapssible member, said shut-off means comprising first and second flexible wall portions of said heating chamber collapsible member, said first and second flexible wall portions being juxtaposed to one another and arranged to be free to move between an open, separated position and a closed, abutting position, and said outlet of said heating chamber collapsible member being positioned in said first flexible wall portion so that when the amount of fluid being withdrawn from said heating chamber collapsible member exceeds the amount of fluid being introduced into said heating chamber collapsible member and the amount of fluid in said heating chamber collapsible member falls below a predetermined value, said first and second flexible wall portions are caused to move towards said closed, abutting position whereby said second flexible wall portion closes said outlet in said first flexible wall portion.

5. The dialysis system of claim 4 further including second pump means for pumping dialysis fluid to said heating chamber collapsible member through said first fluid conducting means.

6. The dialysis system of claim 5 further including pressure stabilizing means responsive to the pressure in said first fluid conducting means for controlling said second pump means to maintain a substantially constant pressure in said first fluid conducting means.

7. The dialysis system of claim 6 wherein said pressure stabilizing means comprises pressure measuring means for measuring the pressure in said first fluid conducting means and control means for controlling said second pump means, said control means being responsive to the pressure measured by said pressure measuring means to control said second pump means so as to maintain the pressure measured by said pressure measuring means substantially constant.

8. The dialysis system of claim 7 further including means for preventing dialysis fluid in said first fluid conducting means from coming into contact with said pressure measuring means.

9. The dialysis system of claim 4 wherein said flexible wall portions are planar and parallel to one another.

10. The dialysis system of claim 4 further including pressure stabilizing means responsive to the pressure in said second fluid conducting means for controlling said first pump means to maintain a substantially constant pressure in said second fluid conducting means when said shut-off means terminates the flow of fluid from said heating chamber collapsible member.

11. The dialysis system of claim 10 wherein said pressure stabilizing means comprises pressure measuring means for measuring the pressure in said second fluid conducting means, and control means for controlling said first pump means, said control means being responsive to the pressure measured by said pressure measuring means to control said first pump means so as to maintain the pressure measured by said pressure measuring means substantially constant.

12. The dialysis system of claim 11 further including means for preventing dialysis fluid in said second fluid conducting means from coming into contact with said pressure measuring means.

13. The dialysis system of claim 4 wherein said first fluid conducting means, said second fluid conducting means and said shut-off means are disposable.

14. The dialysis system of claim 13 wherein the source of dialysis fluid comprises a receptacle containing dialysis fluid.

15. The dialysis system of claim 14 wherein said second fluid conducting means communicates with said receptacle downstream of said dialyzer, and wherein said receptacle further includes regeneration means for cleaning dialysis fluid that has been conducted through said dialyzer.

16. The dialysis system of claim 14 wherein said second fluid conducting means communicates with said receptacle downstream of said dialyzer, and wherein said receptacle includes means for collecting ultrafiltrate from said dialyzer during ultrafiltration.

17. The dialysis system of claim 16 wherein said means for collecting ultrafiltrate includes a spillway for said receptacle positioned at substantially the same elevation as the elevation of dialysis fluid in said receptacle prior to operation of said dialysis system, and a container for collecting run-off from said spillway, so that any ultrafiltrate conducted to said receptacle will run off said spillway and into said container.

18. The apparatus of claim 14 wherein said receptacle includes means for emptying said receptacle of dialysis fluid, and wherein said receptacle is disposable.

19. The apparatus of claim 4 wherein said heating chamber collapsible member includes temperature measuring means for measuring the temperature of dialysis fluid in said heating chamber collapsible member and control means responsive to the temperature measured by said temperature measuring means for controlling said heating means in order to maintain a desired temperature of dialysis fluid in said heating chamber collapsible member.

* * * * *